United States Patent [19]

Nishimura et al.

[11] Patent Number: 4,521,631

[45] Date of Patent: Jun. 4, 1985

[54] PROCESS FOR PRODUCING ACETALDEHYDE

[75] Inventors: Yasuyuki Nishimura; Mutsuo Yamada; Yoshijiro Arikawa; Taiji Kamiguchi; Takanori Kuwahara; Hirotoshi Tanimoto, all of Kure, Japan

[73] Assignee: Babcock-Hitachi Kabushiki Kaisha, Tokyo, Japan

[21] Appl. No.: 620,336

[22] Filed: Jun. 13, 1984

[30] Foreign Application Priority Data

Jun. 13, 1983 [JP] Japan ................................ 58-104291
Mar. 5, 1984 [JP] Japan ................................ 59-41800

[51] Int. Cl.$^3$ ....................... C07C 45/28; C07C 45/33
[52] U.S. Cl. .................................... 568/478; 568/470; 568/475; 568/489
[58] Field of Search ................. 568/478, 489, 470, 475

[56] References Cited

U.S. PATENT DOCUMENTS

| | | | |
|---|---|---|---|
| 3,202,717 | 8/1965 | Kummer | 568/478 |
| 3,471,532 | 10/1969 | Young | 568/478 |
| 3,485,877 | 12/1969 | Hargis et al. | 568/478 |
| 4,311,563 | 1/1982 | Opavsky et al. | 568/478 |

FOREIGN PATENT DOCUMENTS

| | | | |
|---|---|---|---|
| 6523 | 1/1980 | European Pat. Off. | 568/478 |
| 24451 | 6/1974 | Japan | 568/478 |

*Primary Examiner*—Werren B. Lone
*Attorney, Agent, or Firm*—Beall Law Offices

[57] ABSTRACT

A process for producing acetaldehyde from ethylene under mild reaction conditions, selectively and with high yield is provided, which process comprises preparing a composite catalyst comprising a complex of a transition metal capable of forming an oxygen complex by coordination of oxygen molecule with the metal ion of the transition metal, and a complex of a transition metal capable of forming an ethylene complex by coordination of ethylene with the metal ion of the transition metal, and oxidizing ethylene activated by forming the ethylene complex with the combined oxygen in the oxygen complex, activated by forming the oxygen complex.

11 Claims, No Drawings

PROCESS FOR PRODUCING ACETALDEHYDE

BACKGROUND OF THE INVENTION

1. Field of the Invention

This invention relates to a process for producing acetaldehyde, and more particularly it relates to a process for producing acetaldehyde by oxygen-oxidizing ethylene in the presence of a metal complex catalyst.

2. Description of the Prior Art

Acetic acid and aldehydes as basic chemicals for petrochemical industry have been produced by oxidation reactions of the corresponding raw materials. Such oxidation reactions occupy an important position in reaction processes in the field of petrochemical industry. These oxidation reactions have so far been carried out at high temperatures and high pressures, but improvement of reaction selectivity and yield is becoming important problem to be settled.

Acetaldehyde is an important, basic material for production of many organic substances, and its derivatives including many compounds such as acetic acid, acetic esters, etc. As for processes for producing acetaldehyde, the acetylene hydration process, ethanol dehydrogenation process and the ethylene direct oxidation process have been practically employed. However, among them, acetylene the hydration process and ethanol dehydrogenation process are no longer used as commercial processes, since a larger amount of byproducts are formed in a large amount due to their severe reaction conditions. In contrast to these processes, a so-called Wacker's process wherein ethylene is used as raw material and palladium chloride (Pd(2)Cl$_2$)-cupric chloride (Cu(2)Cl$_2$) is used as catalyst, has been noted as the process for producing acetaldehyde under mild reaction conditions, and has come to be the main process among current acetaldehyde production processes.

According to the process, a composite catalyst obtained by dissolving Pd(2)Cl$_2$ and Cu(2)Cl$_2$ as catalysts in a hydrochloric acid solution (pH: 0~2) is employed. Ethylene is first oxidized with divalent palladium (Pd(2)) and water H$_2$O to form acetaldehyde (CH$_3$CHO). The reaction is expressed by the following equation wherein water participates in the reaction:

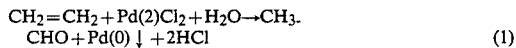

(1)

As seen from the above reaction equation, Pd(2) is reduced to metal palladium Pd(0) which precipitates. This is prevented by making Cu(2)Cl$_2$ coexistent in a large amount, and at the same time, Pd(0) is oxidized into Pd(2) for regeneration according to the following equation:

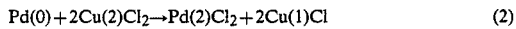

(2)

Further, slightly soluble Cu(1)Cl byproduced at that time is oxygen-oxidized in the copresence of HCl and returned to Cu(2)Cl$_2$ according to the following equation:

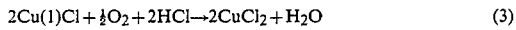

(3)

As described above, by employing a redox system of Pd(2)/Pd(0) and Cu(2)/Cu(1), continuous oxidation of ethylene is rendered possible. However, according to this process, the oxygen molecule is not directly reacted with ethylene as described above, but since a complicated oxidation-reduction reactions of Pd(2)/Pd(0)—Cu(2)/Cu(1) system is utilized, these reactions constitute a reaction rate-determining step. Further, since slightly soluble Pd(0) and Cu(1)Cl are formed midway during the reactions, a concentrated HCl aqueous solution having a high concentration (PH: 0~2) must be used; hence it is necessary to select a corrosion-resistant material. Further, since oxygen has a low solubility in water, it is necessary for accelerating the reaction by increasing its amount dissolved, to carry out the reaction under pressure and heating conditions such as 10 Kg/Cm$^2$ and 100° C. Furthermore, when dissolved oxygen in excess is released into the gas phase, ethylene mixes with oxygen, resulting in a possibility of troubles such as explosion; hence a countermeasure to safety is required.

The object of the present invention is to provide a process for producing acetaldehyde by oxygen-oxidizing ethylene at lower temperatures and lower pressures, selectively and with a high yield.

SUMMARY OF THE INVENTION

The present invention, in short, resides in a process wherein using a composite catalyst comprising a complex of a transition metal capable of forming an oxygen complex by coordination of oxygen molecule with the metal ion of the transition metal, and a complex of a transition metal capable of forming an ethylene complex by coordination of ethylene with the metal ion of the transition metal, ethylene activated by forming the ethylene complex is oxidized with the combined oxygen in the oxygen complex, activated by forming the oxygen complex, to produce acetaldehyde under mild conditions, selectively and with a high yield.

More particularly, the present invention resides in the following process:

In the process for producing acetaldehyde by oxygen-oxidizing ethylene in the presence of a metal complex catalyst, the improvement which comprises using as said metal complex catalyst, a composite catalyst comprising a complex (M$_m$X$_n$.L$_l$) capable of forming an oxygen complex by coordination thereof with oxygen and a complex catalyst (M'$_{m'}$X$_{n'}$'.L'$_{l'}$) capable of forming an ethylene complex by coordination thereof with ethylene (wherein M represents a transition metal belonging to at least one group selected from the group consisting of Group I, Groups IV~VII and the iron group in Group VIII of the periodic table; X represents an anion; ligand L represents an organic phosphorous compound; M' represents a transition metal belonging to platinum group in Group VIII of the periodic table; ligand L' represents at least one compound selected from the group consisting of a nitrile, an organic fluorine compound and an organic phosphorous compound; m, m' and n, n' represent the number of atoms of said transition metals M, M' and said anions X, X', respectively; and l and l' mean a number of said ligands L and L', respectively.

DESCRIPTION OF THE PREFERRED EMBODIMENTS

As to oxygen complexes capable of functioning as an effective oxidizing agent for oxidation reaction of various kinds of organic substances, various studies have been made on Cu(1)-protein and Fe(2)-protein in living bodies. However, examples of oxygen complexes capable of being utilized on a commercial scale are very few. The present inventors have made extensive research on stable oxygen complexes applicable to oxidation of organic substrates with safety. As a result, it has been found that in a representative example, a solution of a complex (Cu(1)Cl. hmpa) of cuprous chloride (Cu(1)Cl) with hexamethylphosphoramide (hmpa; another name, tris(dimethylamino) phosphine oxide) (Japanese patent application laid-open Nos. 56-118720 and 57-19017), as disclosed as an absorbing solution for carbon monoxide (CO), reacts with oxygen in a molar ratio of 2:1 in contact therewith to form the following oxygen complex:

$$2Cu(1)Cl.hmpa + O_2 \rightarrow (Cu(1)Cl.hmpa)_2.O_2 \quad (4)$$

The fact that such oxygen coordinated with the transition metal has been activated is the same as in the case of oxygen complex of Cu(1)-protein or Fe(2)-protein. Such a complex as Cu(1)Cl.hmpa can be expressed by the general formula $M_mX_n.L_l$ where m=1, n=1 and l=1 are applied. Further, for example, in the case where Ti(3) or V(3) constitutes a central metal and the anion is $Cl^-$, the resulting complex is $Ti(3)Cl_3.hmpa$ or $V(3)Cl_3.hmpa$ (m=1, n=3 and l=1 are applied to the above formula).

The above new complexes are so stable that boiling at 100° C. is required for oxidizing Cu(1) into Cu(2) by the combined oxygen. Further, the oxygen once absorbed in the form of the oxygen complex is not easily separated even by heating or deaeration under reduced pressure; hence the absorption is irreversible. Due to this specific feature of the complex, after it has been contacted with pure oxygen or air to form an oxygen complex, it becomes possible to remove physically dissolved free oxygen from the oxygen complex solution by heating or deaeration in vacuo; hence this results in a great effectiveness in the aspect of safety. Another specific feature of the complex is that oxygen is selectively absorbed from air to form all the same oxygen complex as in the case of pure oxygen.

According to the present invention, ethylene is oxidized with the combined oxygen activated by forming an oxygen complex, as described above, and if ethylene is also activated by formation of an ethylene complex, it is possible to make the temperature and pressure of the present oxidation reaction both lower. The present inventors have made studies on various complexes of transition metals belonging to platinum group. In the case of palladium chloride $Pd(2)Cl_2$ as a representative example, this compound forms a complex having two molecules of hmpa coordinated therewith, as shown by the following equation, and well dissolves therein:

$$Pd(2)Cl_2 + 2hmpa \rightleftharpoons Pd(2)Cl_2.(hmpa)_2 \quad (5)$$

This complex can be expressed by the general formula $M'_{m'}X_{n'}.L'_{l'}$, then m'=1, n'=2 and l'=2 in the above equation.

When ethylene is passed through the complex, an ethylene complex is formed, which reaction is shown in the following equation:

$$Pd(2)Cl_2.(hmpa)_2 + CH_2=CH_2 \rightleftharpoons Pd(2)Cl_2.C_2H_4.hmpa + hmpa \quad (6)$$

However, since the coordination of this ethylene complex is weak, various studies have been made on a complex capable of forming a more stable ethylene complex.

As a result, in a representative example, when a nitrile such as acetonitrile is added as a modifying ligand (an auxiliary complexing agent), to a hmpa complex solution of $Pd(2)Cl_2$, the following new complex is formed:

$$Pd(2)Cl_2.(hmpa)_2 + CH_3CN \rightleftharpoons Pd(2)Cl_2.CH_3CN.hmpa + hmpa \quad (7)$$

When ethylene is passed through this complex, a stable ethylene complex is formed as shown by the following equation:

$$Pd(2)Cl_2.CH_3CN.hmpa + CH_2=CH_2 \rightleftharpoons Pd(2)Cl_2.C_2H_4.CH_3CN + hmpa \quad (8)$$

With such a stable ethylene complex, ethylene is notably activated.

Such a formation of a complex of the above new Pd(2) complex with ethylene has been studied according the gas absorption method. As a result, a hmpa solution of acetonitrile absorbed 0.07 mol/l of ethylene at 20° C. and under an ethylene partial pressure of 1 atm, whereas the solution of $Pd(2)Cl_2.CH_3CN.hmpa$ complex absorbed 0.10 mol/l of ethylene which is about 1.5 times the above amount. Although ethylene is absorbed in a large amount even only due to the solvent used therein since the system is non-aqueous, the above difference in the amount of ethylene absorbed evidences that a new complex of a Pd(2) complex with ethylene has been formed.

Thus the present invention has been completed wherein ethylene, coordinated with a Pd(2) complex in the form of an ethylene complex and activated thereby, is oxidized with the combined oxygen contained in the above oxygen complex, under mild conditions, to produce acetaldehyde.

According to the present invention, typically, a two-component system catalyst consisting of Cu(1)Cl.hmpa complex and $Pd(2)Cl_2.CH_3CN.hmpa$ complex is dissolved in liquid hmpa (also as a ligand) or toluene etc., each as a solvent, followed by passing air through the resulting solution so as to give an adequate oxygen complex concentration, as described below, to form an oxygen complex, removing excess oxygen by heating, deaeration or the like, passing ethylene through the resulting complex, to form an ethylene complex, and oxidizing the thus activated ethylene with the combined oxygen contained in the oxygen complex, at a temperature close to room temperature to produce acetaldehyde nearly quantitatively.

This oxidation reaction is expressed by the following equation when hmpa is used as a complexing agent and as a solvent:

$$(Cu(1)Cl.hmpa)_2O_2 + 2Pd(2)Cl_2.C_2H_4.CH_3CN + hmpa$$
$$\rightarrow 2CH_3CHO + 2Cu(1)Cl.hmpa + 2Pd(2)Cl_2.CH_3CN.hmpa \quad (9)$$

As described above, ethylene coordinated with Pd(2) complex is oxidized with oxygen molecule coordinated with Cu(1) complex. Thus, the valences of the metal ions in the complexes are unchanged, and water ($H_2O$) does not participate in the acetaldehyde-producing reactions. In the present invention, however, it does not matter if water is coexistent, so long as its amount is in the range where no precipitate is formed. Even in view of this fact, the present process is quite different from Wacker's process wherein an oxidation-reduction reaction by way of Pd(2) ion and water is applied. As for the complex of the present invention, where air is passed therethrough after completion of the reaction, the oxygen complex is again formed to make it possible to reuse the complex as the catalyst for ethylene oxidation. Further, the Pd(2) complex, too, may be repeatedly used as the catalyst for ethylene activation.

Thus, according to the present invention, since the reaction substrate is activated in the form of a complex, it is possible to attain a reaction rate superior to those according to the conventional process, under normal pressures and at a low temperature close to room temperature.

As for the $M_mX_n$ in the complex catalyst ($M_mX_n.L_l$) capable of forming the oxygen complex in the composite catalyst system, salts of Cu or Ag of Group I, Ti or Zr of Group IV, V or Nb of Group V, Cr, Mo or W of Group VI, Mn of Group VII and Fe, Co or Ni of Group VIII, of the periodic table are preferred, and halides of Cu(1), Ti(3) or V(3) are particularly preferred. As for X in the complex catalyst, $Cl^-$, $Br^-$, $I^-$, $BF_4^-$, $PF_4^-$, $PF_6^-$, $SO_4^{2-}$ and $CH_3COO^-$ are preferable. The ligand L is preferred to be organic phosphorous compounds represented by phosphoric acid derivatives such as triphenylphosphine oxide, hexamethylphosphoramide and mono-, di- and triesters formed by reaction of phosphoric acid with methanol, ethanol or the like, further dimethyl methylphosphinate, methyl dimethylphosphinate, and further phosphorous acid derivatives such as mono-, di- or triesters formed by reaction of phosphorous acid with methanol, ethanol, or the like, phenyl phosphonous acid esters, dimethylphosphinic acid esters, triethylphosphine, triphenylphosphine, and among them hexamethylphosphoramide (hmpa) is particularly preferred.

On the other hand, the $M'_m'X_n'$ in the complex catalyst ($M'_m'X_n'.L'_l'$) capable of forming the ethylene complex is preferred to be salts of lower valence ions of transition metals belonging to platinum group in Group VIII, and particularly preferred to be halides of Pd(2) or Pt(2). The ligand L' is preferred to be a nitrile such as acetonitrile, propionitrile, benzonitrile, tolunitrile, etc., the above organic phosphorous compounds or organic fluorine compounds such as fluorinated toluene, benzotrifluoride, etc., and particularly preferred to be a nitrile.

As for the solvent used in the case where the above reaction is carried out in a solution state, those which dissolve the composite complex and at the same time are easily separated from the resulting acetaldehyde (b.p. 21° C./760 mmHg) are preferred, and there may be used at least one kind selected from various solvents such as n-hexane, toluene, cyclohexane, methyl isobutyl ketone, cyclohexanone, ethanol, ethylene glycol, butyl acetate, propylenecarbonate, chloroform, chlorobenzene, pyridine, tetrahydrofuran, etc., or mixtures of the foregoing, or L or L' itself if the ligand is liquid.

In addition, as to acetaldehyde as product, oxidation may be further advanced by the combined oxygen in the oxygen complex to form acetic acid, depending on the reaction conditions. In such a case, the product is a mixture of acetaldehyde with acetic acid, and acetaldehyde may be separated easily from acetic acid through distillation.

In the present invention, in order to improve the selectivity of acetaldehyde production, it is preferred to make a basic compound coexistent in the reaction system, as described later in Examples. Examples of the basic compound are sulfolane, dimethylsulfolane, dimethylsulfoxide, dimethylformamide, trimethylmethane, dimethylsulfone, etc..

The present invention will be described below in more detail by way of Examples. The values of gas volume therein are those under standard conditions.

EXAMPLE 1

Into a 1 l capacity reactor were fed cuprous chloride (hereinafter referred to as Cu(1)Cl) (5 g, 50 mmols) and hmpa (325 g) to prepare Cu(1)Cl.hmpa complex solution (330 ml). Separately, into a test tube with a ground stopper were fed palladium chloride (Pd(2)Cl$_2$) (1.3 g, 7 mmols) and acetonitrile (CH$_3$CN) (130 g) to prepare Pd(2)Cl$_2$.(CH$_3$CN)$_2$ complex solution (170 ml). This solution was transferred into the above reactor to prepare a catalyst solution (Cu(1)Cl.hmpa/Pd(2)-Cl$_2$.CH$_3$CN.hmpa/hmpa, CH$_3$CN system) (500 ml) containing Cu(1)Cl (0.1 mol/l) and Pd(2)Cl$_2$ (0.015 mol/l). When air (800 ml) was passed through this solution at 25° C. under the atmospheric pressure, oxygen (147 ml, 6 mmols) was absorbed to obtain a solution of an oxygen complex having a concentration of 0.01 mol/l. Thereafter, when nitrogen gas was passed therethrough, only the oxygen physically dissolved in the liquid phase of the reactor was removed, but separation of oxygen from the combined oxygen was not observed. Namely, the oxygen absorption is irreversible. This is very advantageous with respect to safety in practical processes.

After this operation, when ethylene (2,200 ml) was passed therethrough similarly at 25° C. under the atmospheric pressure, ethylene (1,960 ml, 80 mmols) was absorbed to give an ethylene concentration in the solution of 0.16 mol/l.

Just thereafter the solution was warmed to 60° C. and subjected to reaction for 30 minutes, and followed by cooling the reaction solution. After analyzing the resulting product according to gas chromatography, CH$_3$CHO (0.4 g, 9.6 mmols) was produced.

The reaction of the ethylene complex with the oxygen complex is carried out according to the above equation (9), and in this Example, the ethylene complex is present in excess relative to the oxygen complex. Thus, the conversion of ethylene into acetaldehyde in this Example was 86% based on the combined oxygen in the oxygen complex.

EXAMPLE 2

Example 1 was repeated except that acetonitrile was replaced by benzonitrile. The yield of acetaldehyde was 98%, that is, a higher yield than that in the case of acetonitrile was obtained.

EXAMPLE 3

The reaction in Example 2 was carried out for 2 hours. The yield of CH$_3$CHO lowered down to 93%, and acetic acid (5%) was formed.

EXAMPLE 4

Example 2 was repeated except that hmpa (105 g), benzonitrile (15 g) and sulfolane (480 g) were added and reaction was carried out for one hour. The yield of CH$_3$CHO amounted to 98%, and even after additional 5 hours, oxidation into acetic acid was not observed.

EXAMPLE 5

Reaction was carried out under the same conditions as in Example 4 except that Pd(2)Cl$_2$ in Example 1 was replaced by Pt(2)Cl$_2$. The yield of acetaldehyde was 99%, that is, in this case, it was also observed that the oxidation reaction was carried out nearly quantitatively.

EXAMPLE 6

Example 2 was repeated except that 85 g of hmpa was used and toluene (275 g) was added, to study the effect of solvent. The yield of acetaldehyde was 97%, that is, almost the same as in the case of Example 2.

EXAMPLE 7

Example 2 was repeated except that Cu(1)Cl was replaced by cuprous bromide (Cu(1)Br). The yield of acetaldehyde was 96%.

EXAMPLE 8

Example 2 was repeated except that Cu(1)Cl was replaced by cuprous iodide (Cu(1)I). The yield of acetaldehyde was 97%.

EXAMPLE 9

Example 4 was repeated except that Cu(1)Cl was replaced by V(3)Cl$_3$. The yield of CH$_3$CHO was 69%. Further, in the case of replacement by Ti(3)Cl$_3$, the yield of CH$_3$CHO was 72%.

EXAMPLE 10

Example 4 was repeated except that benzonitrile was replaced by benzotrifluoride. The yield of CH$_3$CHO was 89%.

EXAMPLE 11

Beads of a styrene-divinylbenzene copolymer of macroreticular form (Amberlite (Trademark) XA D-4 made by Organo Company, particle diameter 1mm$\phi$; specific surface area 700~800 m$^2$/g) (50 ml) was impregnated with a catalyst solution containing the oxygen complex having the composition shown in Example 4, followed by filtration by means of suction to prepare a granular catalyst, which was then filled in a hard glass reaction tube having an inner diameter of 20 mm$\phi$, followed by heating it to 60° C., then passing ethylene (1 l/min, SV=1,200 h$^{-1}$) and analyzing acetaldehyde contained in the exit gas. The resulting product was acetic acid alone, and its yield based on ethylene was 4% till two hours since the start of the reaction. Thereafter the exit gas was recycled to obtain an acetaldehyde yield of 87% based on the combined oxygen in the oxygen complex. Further, the feed of ethylene was once stopped, followed by passing air therethrough to regenerate the combined oxygen consumed by the reaction and then again carrying out oxidation experiment under the above conditions to obtain similar results.

From the foregoing, it is evident that even when the complex catalyst of the present invention is supported on a carrier, the reaction by means of the combined oxygen in the oxygen complex advances.

In addition, it was possible to use other porous carriers such as silicates, active carbon, porous glass, etc.. Further, as for the treating process after the impregnation of the catalyst solution, various processes other than filtration by means of suction may be employed such as passing of heated gas, low temperature calcination, etc.

COMPARATIVE EXAMPLE 1

In Examples 1, 2, 3, 4 and 10, similar catalyst solutions were prepared except that neither nitrile nor organic fluorine compound was added, followed by carrying out the same operations. As a result, any of the CH$_3$CHO yields were 0.1% or less. Thus it was found that nitriles or organic fluorine compounds as a modifying ligand contributed greatly to ethylene activation.

COMPARATIVE EXAMPLE 2

Into the same reactor as in Example 1 were fed Pd(2)Cl$_2$ (1.3 g) and hmpa (325 g) to prepare a hmpa solution of Pd(2)Cl$_2$.(hmpa)$_2$. Ethylene was passed through the solution in the same manner as in Example 1 but without passing air therethrough, to carry out reaction under the same conditions as in Example 1 (60° C., 30 minutes), but ethylene was utterly not oxidized. Further, no precipitate of metal palladium (Pd(0)) was formed; thus it was evidenced that oxidation by means of Pd(2) ion did not occur.

COMPARATIVE EXAMPLE 3

Cu(1)Cl (5 g) was added to the complex solution prepared in Comparative Example 2, to prepare a catalyst solution consisting of Cu(1)Cl/Pd(2)Cl$_2$/hmpa, followed by carrying out the same procedure and reaction as in Comparative Example 2, but ethylene oxidation was utterly not observed. Thus it was evidenced that it was necessary to pass air through the solution to thereby form an oxygen complex.

COMPARATIVE EXAMPLE 4

Benzonitrile was added to the complex solution prepared in Comparative Example 3, followed by carrying out the same procedure and reaction as in Comparative Example 1. In this case, too, since air was not passed, ethylene oxidation was not observed.

COMPARATIVE EXAMPLE 5

In Comparative Example 2, air was passed, but ethylene was utterly not reacted. This evidences that oxidation reaction by way of free oxygen does not occur in the present system.

In view of Comparative Examples 2 and 3, it is evidenced that the present invention is entirely different from the process for producing acetaldehyde from ethylene by the use of Pd(2)Cl-Cu(2)Cl redox system as catalyst.

In addition, when air was passed through the catalyst solution containing the ethylene complex in Comparative Example 4, acetaldehyde was produced with a high yield as in the above Examples.

From the foregoing, it is evident that unlike conventional processes, the present invention is a new process for producing acetaldehyde by oxidizing the combined ethylene activated by formation of an ethylene complex, with the combined oxygen activated by formation of an oxygen complex.

According to the present invention, ethylene is not directly contacted with oxygen gas, but ethylene and oxygen each coordinated with a transition metal ion and activated thereby through a specified composite catalyst system are reacted together; hence the reaction can be carried out at low temperatures and low pressures such as nearly room temperature and the atmospheric pressure to thereby produce the objective acetaldehyde selectively and with high yield. Further, according to the present invention, since the amount of byproducts is small, it is possible to simplify the production steps including the subsequent purification step. Further, even when air is used as oxygen source, oxygen is selectively absorbed; hence the same effectiveness as in the case of use of pure oxygen gas is obtained. Furthermore, since the oxygen absorption is irreversible, it is possible to easily remove excess free oxygen after the oxygen complex has been formed; hence this process is very advantageous also in the aspect of safety.

What we claim is:

1. In the process for producing acetaldehyde by oxygen-oxidizing ethylene in the presence of a metal complex catalyst, the improvement which comprises using as said metal complex catalyst, a composite catalyst comprising a complex ($M_m X_n \cdot L_l$) capable of forming an oxygen complex by coordination thereof with oxygen and a complex catalyst ($M'_{m'} X_{n'} \cdot L'_{l'}$) capable of forming an ethylene complex by coordination thereof with ethylene, wherein M represents a transition metal belonging to at least one group selected from the group consisting of Group I, Groups IV~VII and iron group in Group VIII of the periodic table; X represents an anion; ligand L represents an organic phosphorous compound; M' represents a transition metal belonging to platinum group in Group VIII of the periodic table; ligand L' represents at least one compound selected from the group consisting of a nitrile, an organic fluorine compound and an organic phosphorous compound; m, m' and n, n' represent a number of atoms of said transition metals M, M' and said anions X, X', respectively; and l and l' represent a number of said ligands L and L', respectively.

2. A process according to claim 1, wherein said m, n, l, m', n' and l' each represent a number in the range of 1 to 4.

3. A process according to claim 1, wherein said X is an anion selected from the group consisting of $Cl^-$, $Br^-$, $I^-$, $BF_4^-$, $PF_6^-$, $SO_4^{2-}$ and $CH_3COO^-$.

4. A process according to claim 1, wherein said organic phosphorous compound as said ligands L, L' is at least one compound selected from the group consisting of alkoxy, alkyl and amide derivatives of phosphorous acid, and phosphoric acid.

5. A process according to claim 1, wherein as a solvent for said complex capable of forming the oxygen complex and for said complex capable of forming the ethylene complex, there is used at least one compound selected from the group consisting of aliphatic, aromatic and alicyclic hydrocarbons, oxygen-containing organic compounds, organic halide compounds, and nitrogen-containing organic compounds.

6. A process according to claim 1, wherein said ligand L or L' is liquid and L or L' itself is used as a solvent for said complexes.

7. A process according to claim 1, wherein oxygen or air is passed through a solution of said composite catalyst to form said oxygen complex and said ethylene complex to thereby react the both together.

8. A process according to claim 1, wherein a porous carrier is impregnated with a solution of said composite catalyst and oxygen or air and ethylene are passed therethrough to oxidize ethylene with the combined oxygen in said oxygen complex.

9. A process according to claim 1, wherein a basic (or electron-donating) compound selected from the group consisting of sulfolane, dimethylsulfolane, dimethylsulfoxide and dimethylformamide is added to a solution of said complex catalyst.

10. A process according to claim 1, wherein a basic (or electron-donating) compound selected from the group consisting of sulfolane, dimethylsulfolane, dimethylsulfoxide and dimethylformamide is used as a solvent for said composite catalyst.

11. A process according to claim 1, wherein $M_n X_n$ is CuCl, L is hexamethylphosphoramide, $M'_m$, $X_n$, is $PdCl_2$ and L' is acetonitrile.

* * * * *